United States Patent
Choi et al.

(10) Patent No.: US 10,238,320 B2
(45) Date of Patent: *Mar. 26, 2019

(54) METHOD AND APPARATUS FOR CALCULATING AMOUNT OF EXERCISE PERFORMED

(71) Applicant: Samsung Electronics Co., Ltd., Suwon-si (KR)

(72) Inventors: Chang Mok Choi, Seoul (KR); Byung Hoon Ko, Hwaseong-si (KR); Tak Hyung Lee, Seoul (KR); Kun Soo Shin, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 18 days.

This patent is subject to a terminal disclaimer.

(21) Appl. No.: 15/255,212

(22) Filed: Sep. 2, 2016

(65) Prior Publication Data

US 2017/0007162 A1 Jan. 12, 2017

Related U.S. Application Data

(63) Continuation of application No. 14/058,965, filed on Oct. 21, 2013, now Pat. No. 9,445,753.

(30) Foreign Application Priority Data

Oct. 30, 2012 (KR) .................. 10-2012-0121163

(51) Int. Cl.
*A61B 5/11* (2006.01)
*A61B 5/00* (2006.01)
(Continued)

(52) U.S. Cl.
CPC .......... *A61B 5/1126* (2013.01); *A61B 5/0531* (2013.01); *A61B 5/112* (2013.01);
(Continued)

(58) Field of Classification Search
CPC ..... A61B 5/1126; A61B 5/704; A61B 5/4866; A61B 5/6801
See application file for complete search history.

(56) References Cited

U.S. PATENT DOCUMENTS

| 4,367,752 A | 1/1983 | Jimenez et al. |
| 5,713,367 A | 2/1998 | Arnold et al. |

(Continued)

FOREIGN PATENT DOCUMENTS

| CN | 1093563 A | 10/1994 |
| CN | 1909828 A | 2/2007 |

(Continued)

OTHER PUBLICATIONS

S. Patterson et al., "Automated physical activity monitoring: validation and comparison with physiological and self-report measures," *Psychophysiology*, vol. 30, No. 3, May 1993, pp. 296-305 (abstract only).

(Continued)

*Primary Examiner* — Daniel L Cerioni
*Assistant Examiner* — Yasmeen S Warsi
(74) *Attorney, Agent, or Firm* — NSIP Law

(57) ABSTRACT

A method of calculating an amount of exercise performed includes measuring noise based on a relative difference in displacement between a skin of a user and a sensor attached to the skin of the user, and determining a number of steps taken by the user based on the measured noise.

20 Claims, 11 Drawing Sheets

(51) Int. Cl.
*A61B 7/04* (2006.01)
*A61B 5/053* (2006.01)
*A61B 5/22* (2006.01)
*G01C 22/00* (2006.01)
*A63B 24/00* (2006.01)

(52) U.S. Cl.
CPC ............ *A61B 5/1118* (2013.01); *A61B 5/221* (2013.01); *A61B 5/4866* (2013.01); *A61B 5/6801* (2013.01); *A61B 5/7257* (2013.01); *A61B 5/7278* (2013.01); *A61B 7/04* (2013.01); *A63B 24/0062* (2013.01); *G01C 22/006* (2013.01); *A61B 5/7253* (2013.01); *A61B 2562/0204* (2013.01); *A61B 2562/0209* (2013.01); *A63B 2220/17* (2013.01)

(56) References Cited

U.S. PATENT DOCUMENTS

| | | | |
|---|---|---|---|
| 5,989,200 | A | 11/1999 | Yoshimura et al. |
| 2007/0173734 | A1 | 7/2007 | Kim et al. |
| 2009/0177097 | A1* | 7/2009 | Ma .................... A63B 71/0686 600/500 |
| 2010/0234181 | A1 | 9/2010 | Cho et al. |
| 2011/0270049 | A1 | 11/2011 | Katra et al. |
| 2012/0119911 | A1 | 5/2012 | Jeon et al. |
| 2013/0191034 | A1* | 7/2013 | Weast .................... G06F 17/00 702/19 |

FOREIGN PATENT DOCUMENTS

| | | |
|---|---|---|
| CN | 101522104 A | 9/2009 |
| JP | 2001-411 A | 1/2001 |
| JP | 2008-246177 A | 10/2008 |
| JP | 2009-279211 A | 12/2009 |
| JP | 2009279211 A * | 12/2009 |
| KR | 10-2006-0092557 A | 8/2006 |
| KR | 10-2006-0117449 A | 11/2006 |
| KR | 10-2007-0102788 A | 10/2007 |
| KR | 10-2008-0008823 A | 1/2008 |
| KR | 10-2008-0036755 A | 4/2008 |
| KR | 10-0858554 B1 | 9/2008 |
| KR | 10-2010-0048324 A | 5/2010 |
| KR | 10-2011-0070298 A | 6/2011 |
| KR | 10-2011-0118879 A | 11/2011 |
| WO | WO 97/37588 A1 | 10/1997 |
| WO | WO 2004/032715 A2 | 4/2004 |

OTHER PUBLICATIONS

A. Sugimoto et al., "A useful method for measuring daily physical activity by a three-direction monitor," Scandinavian Journal of Rehabilitation Medicine, vol. 29, No. 1, Mar. 1997, pp. 37-42 (abstract only).

H. Kashiwazaki, "Heart Rate Monitoring as a Field Method for Estimating Energy Expenditure as Evaluated by the Doubly Labeled Water Method," Journal of Nutritional Science and Vitaminology, vol. 45, No. 1, Jan. 1999, pp. 79-94, released Apr. 28, 2009.

Y. Liu, "Reduction of Skin Stretch Induced Motion Artifacts in Electrocardiogram Monitoring Using Adaptive Filtering," dissertation submitted to the Faculty of the Graduate School of the University of Maryland, College Park, in partial fulfillment of the requirements for the degree of Doctor of Philosophy, 2007 (142 pages).

N. Ryu et al., "A Calorie Count Application for a Mobile Phone Based on METS Value," Proceedings of the 5th Annual IEEE Communications Society Conference on Sensor, Mesh and Ad Hoc Communications and Networks, 2008 (SECON '08), pp. 583-584, conference held Jun. 16-20, 2008, San Francisco, demo presented on Jun. 18, 2008, http://dx.doi.org/10.1109/SAHCN.2008.77.

"Biopotential Electrodes," PowerPoint presentation, Medical Engineering Laboratory, Soon Chun Hyang University, Asan, Republic of Korea, author unknown, date unknown (32 pages, in Korean, including English abstract).

Ko, Byung-hoon, et al. "Motion artifact reduction in electrocardiogram using adaptive filtering based on halfcell potential monitoring." Engineering in Medicine and Biology Society (EMBC), 34th Annual International Conference of the IEEE, IEEE, Aug./Sep. 2012, pp. 1590-1593.

Extended European Search Report dated Feb. 19, 2014 in counterpart European Patent Application No. 13186048.8. (7 pages in English).

Chinese Office Action dated Feb. 6, 2016 in counterpart Chinese Patent Application No. 201310436584.2 (6 pages in English; 5 pages in Chinese).

Japanese Office Action issued by the Japanese Patent Office dated May 16, 2017 for the corresponding Japanese Patent Application No. 2013-204017. (9 pages in Japanese and 9 pages in English).

* cited by examiner

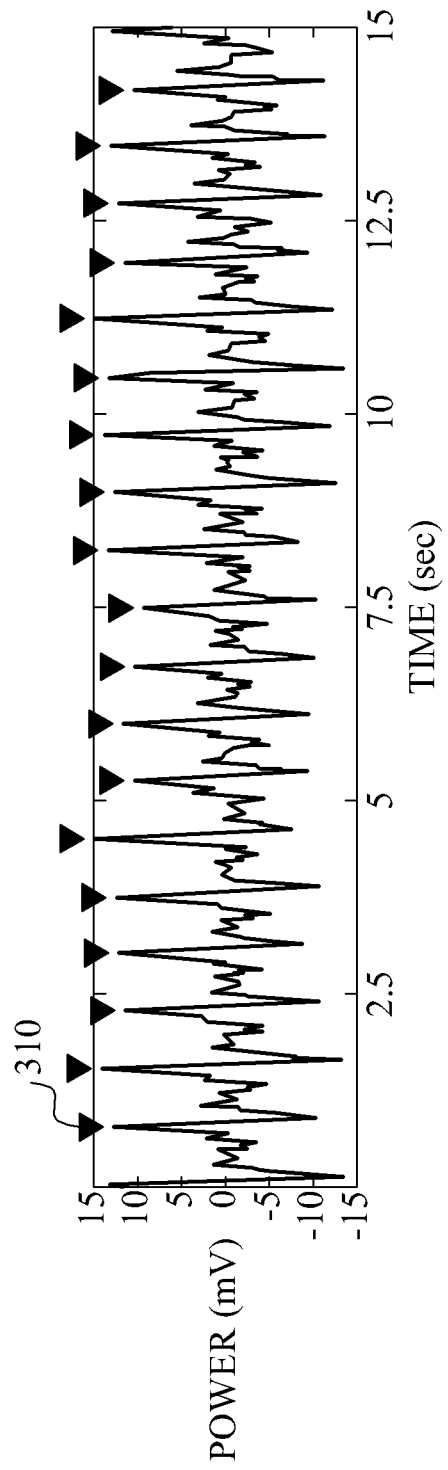

METHOD AND APPARATUS FOR CALCULATING AMOUNT OF EXERCISE PERFORMED

CROSS-REFERENCE TO RELATED APPLICATIONS

This application is a continuation of U.S. patent application Ser. No. 14/058,965, filed on Oct. 21, 2013, now U.S. Pat. No. 9,445,753 issued on Sep. 20, 2016, which claims the benefit under 35 U.S.C. § 119(a) of Korean Patent Application No. 10-2012-0121163, filed on Oct. 30, 2012, in the Korean Intellectual Property Office, the disclosure of which is incorporated herein by reference in its entirety for all purposes.

BACKGROUND

1. Field

The following description relates to a method of calculating an amount of exercise performed by a user based on noise generated between a skin of the user and a sensor.

2. Description of Related Art

Recently, issues such as obesity and being overweight have been garnering attention. Use of an apparatus for measuring an amount of exercise performed by people exercising for overall fitness or to keep in shape may enable an exercise routine to be established. A general apparatus for measuring an amount of exercise performed may include a calorie consumption measuring apparatus. The calorie consumption measuring apparatus may be classified based on a measuring scheme, for example, an accelerometer measuring scheme, a heart rate measuring scheme, and a heart rate-accelerometer measuring scheme.

The accelerometer measuring scheme may use a change in acceleration generated by a movement of a user using an accelerometer sensor. The accelerometer measuring scheme may calculate a number of steps taken by the user from the change in acceleration, and calculate calorie consumption based on the calculated number of steps.

The heart rate measuring scheme may calculate calorie consumption by measuring a number of heartbeats as a user exercises. The heart rate measuring scheme may calculate calorie consumption based on a number of maximum heartbeats and a type of exercise performed by a user, or calculate calorie consumption based on the measured number of heartbeats and user information.

The heart rate-accelerometer scheme may measure an amount of exercise performed by a user using an accelerometer sensor, and measure a number of heartbeats of the user using a heart rate sensor. The heart rate-accelerometer scheme may calculate calorie consumption selectively using the accelerometer measuring scheme and the heart rate measuring scheme by determining a movement pattern of a user, or using the measured amount of exercise and the number of heartbeats.

SUMMARY

In one general aspect, a method of calculating an amount of exercise performed includes measuring noise based on a relative difference in displacement between a skin of a user and a sensor attached to the skin of the user; and determining a number of steps taken by the user based on the measured noise.

The method may further include calculating an amount of exercise performed by the user based on the determined number of steps.

The calculating of the amount of exercise performed by the user may include calculating the amount of exercise of the user based on the determined number of steps and physiological information of the user.

The calculating of the amount of exercise performed by the user may include calculating a speed at which exercise is performed by the user based on the determined number of steps, a stride length of the user, and a duration of exercise performed by the user; and calculating the amount of exercise performed by the user based on the calculated speed at which exercise is performed by the user and a weight of the user.

The calculating of the amount of exercise performed by the user may include calculating the amount of exercise performed by the user using a lookup table (LUT) indicating a relationship between a number of steps taken and an amount of exercise performed, and the determined number of steps.

The amount of exercise performed by the user may include any one or any combination of a number of steps taken over a duration of exercise performed by the user, an amount of energy consumed over the duration of the exercise, and an amount of oxygen consumed over the duration of the exercise.

The measuring of the noise may include measuring noise by detecting, from the sensor, a half cell potential (HCP) generated by the relative difference in displacement between the skin of the user and the sensor.

The measuring of the noise may include measuring noise by detecting, from the sensor, a change of impedance generated by the relative difference in displacement between the skin of the user and the sensor.

The determining of the number of steps taken by the user may include converting the measured noise to a frequency domain; and determining the number of steps taken by the user based on the noise converted to the frequency domain.

The determining of the number of steps taken by user may include identifying a frequency of noise having a greatest value from the noise converted to the frequency domain; and determining the number of steps taken by the user based on the identified frequency and a number of steps corresponding to a single cycle of the noise.

The determining of the number of steps taken by the user may include sampling the measured noise; extracting peaks of the noise from the sampled noise; and determining the number of steps taken by the user based on a number of the extracted peaks.

The extracting of the peaks of the noise may include excluding noise failing to satisfy a predetermined threshold from the sampled noise.

In another general aspect, a non-transitory computer-readable storage medium stores a program for controlling a computer to perform the method described above.

In another general aspect, an apparatus for calculating an amount of exercise performed includes a noise measuring unit configured to measure noise based on a relative difference in displacement between a skin of a user and a sensor attached to the skin; and a step count determining unit configured to determine a number of steps taken by the user based on the measured noise.

The apparatus may further include an amount of exercise performed calculating unit configured to calculate an amount of exercise performed by the user using the determined number of steps.

The amount of exercise performed calculating unit may be further configured to calculate the amount of exercise performed by the user using a lookup table (LUT) indicating a relationship between a number of steps taken and an amount of exercise performed, and the determined number of steps.

The amount of exercise performed calculating unit may be further configured to calculate the amount of exercise performed by the user based on the determined number of steps and physiological information of the user.

The amount of exercise performed calculating unit may be further configured to calculate a speed at which exercise is performed by the user based on the determined number of steps, a stride length of the user, and a duration of exercise performed by the user; and calculate the amount of exercise performed by the user based on the calculated speed at which exercise is performed by the user and a weight of the user.

The noise measuring unit may be further configured to measure noise by detecting, from the sensor, a half cell potential (HCP) generated by the relative difference in displacement between the skin of the user and the sensor.

The noise measuring unit may be further configured to measure noise by detecting, from the sensor, a change of impedance generated by the relative difference in displacement between the skin of the user and the sensor.

The step count determining unit may be further configured to convert the measured noise to a frequency domain; and determine the number of steps taken by the user based on the noise converted to the frequency domain.

The step count determining unit may be further configured to sample the measured noise; extract peaks of the noise from the sampled noise; and determine the number of steps taken by the user based on a number of the extracted peaks.

In another general aspect, a method of calculating an amount of exercise performed by user includes measuring noise produced by movement of the user while performing exercise; and determining a number of steps taken by the user based on the measured noise.

The measuring may include measuring the noise using a sensor attached to a skin of the user; and the noise may produced by relative movement between the sensor and the skin caused by the movement of the user while performing exercise.

The determining of the number of steps may include extracting information from the measured noise; and determining the number of steps taken by the user based on the extracted information.

Other features and aspects will be apparent from the following detailed description, the drawings, and the claims.

BRIEF DESCRIPTION OF THE DRAWINGS

FIGS. 3A and 3B are graphs illustrating examples of noise measured from a sensor.

DETAILED DESCRIPTION

Figure 1:
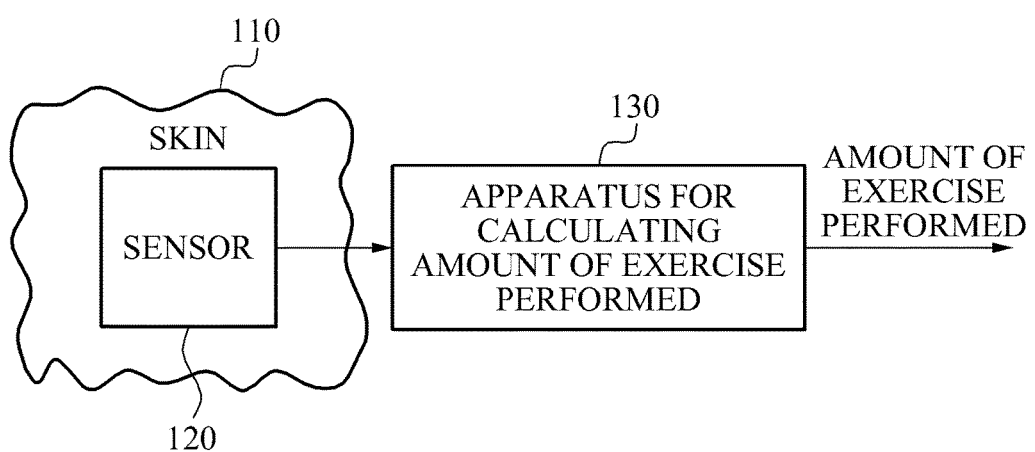
FIG. 1 is a diagram illustrating an example of an apparatus for calculating an amount of exercise performed.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 is a diagram illustrating an example of an apparatus 130 for calculating an amount of exercise performed. Referring to FIG. 1, the apparatus 130 for calculating an amount of exercise performed measures noise based on a relative difference in displacement between a skin 110 of a user and a sensor 120 attached to the skin 110. The sensor 120 may detect noise generated by exercise performed by the user by being attached to the skin 110 of the user.

For example, the sensor 120 may detect noise generated by relative difference in displacement between the skin 110 of the user and the sensor 120 in a form of a half cell potential (HCP) through an electrode. The HCP may refer to a potential difference between an electrode and an electrolyte when a chemical reaction and an electrical power are in equilibrium. In particular, the sensor 120 may detect the potential difference between the electrode of the sensor 120 and the skin 110.

The sensor 120 detects, in a form of an impedance, noise to which a change in electrical properties of skin generated by the relative difference in displacement between the skin 110 of the user and the sensor 120 is applied. For example, the sensor 120 may be an impedance sensor that measures impedance in a body by being attached to the skin 110 of the user. The sensor 120 may detect noise generated by exercise performed by the user, and the noise may be output in a form of an impedance change.

When the user exercises, a relative difference in displacement due to a movement of the user may occur between the skin 110 of the user and the sensor 120 attached to the skin 110 of the user. For example, when the user exercises, a distance travelled by the skin 110 of the user and a distance travelled by the sensor 120 may not be identical, and such a difference in distance may result in a difference in displacement.

The apparatus 130 for calculating an amount of exercise performed determines a number of steps taken by the user based on measured noise. The apparatus 130 for calculating an amount of exercise performed may determine the number of steps taken by the user during exercise by analyzing the measured noise.

For example, the apparatus 130 for calculating an amount of exercise performed extracts peaks of noise, and determines a number of steps taken based on a number of peaks extracted. For example, the apparatus 130 for calculating an amount of exercise performed may determine the number of steps taken by the user by multiplying the number of peaks by a cycle of noise or a number of steps per peak.

The apparatus 130 for calculating an amount of exercise performed may determine a number of steps by analyzing a frequency of noise converted to a frequency domain. For example, the apparatus 130 for calculating an amount of exercise performed may determine the number of steps by identifying a frequency having a greatest value in the noise converted to the frequency domain.

The apparatus 130 for calculating an amount of exercise performed calculates an amount of exercise performed by the user based on the determined number of steps. For example, the apparatus 130 for calculating an amount of exercise performed may calculate a number of steps taken, an amount of oxygen consumed, an amount of energy consumed such as a calorie, and other parameters related to an amount of exercise being performed during exercise performed by the user based on the number of steps.

For example, the apparatus 130 for calculating an amount of exercise performed calculates an amount of exercise performed by applying the determined number of steps to an amount of exercise performed calculating model. The amount of exercise performed calculating model may refer to a general calculating model used to calculate an amount of exercise performed, such as an amount of energy consumed, an amount of oxygen consumed, and other parameters related to an amount of exercise being performed. The apparatus 130 for calculating an amount of exercise performed may calculate an amount of exercise irrespective of exercise conditions, for example, an emotional state, digestion, intake of nicotine or caffeine by a user, a temperature, and other exercise conditions.

The apparatus 130 for calculating an amount of exercise performed calculates an amount of exercise performed using noise generated between the skin 110 of the user and the sensor 120 attached to the skin 110 of the user. Accordingly, use of an additional acceleration sensor for calculating an amount of exercise performed by the user may not be required by the apparatus 130 for calculating an amount of exercise performed. An amount of power consumed in calculating an amount of exercise performed may be reduced since the apparatus 130 for calculating an amount of exercise performed may measure noise using a single amplifier and without using an acceleration sensor.

The apparatus 130 for calculating an amount of exercise performed provides a user with an amount of exercise performed calculated in real time via an output device. The user may exercise according to a well-organized routine, or adjust a current exercise difficulty or a duration of exercising based on the amount of exercise performed information provided.

Figure 2:
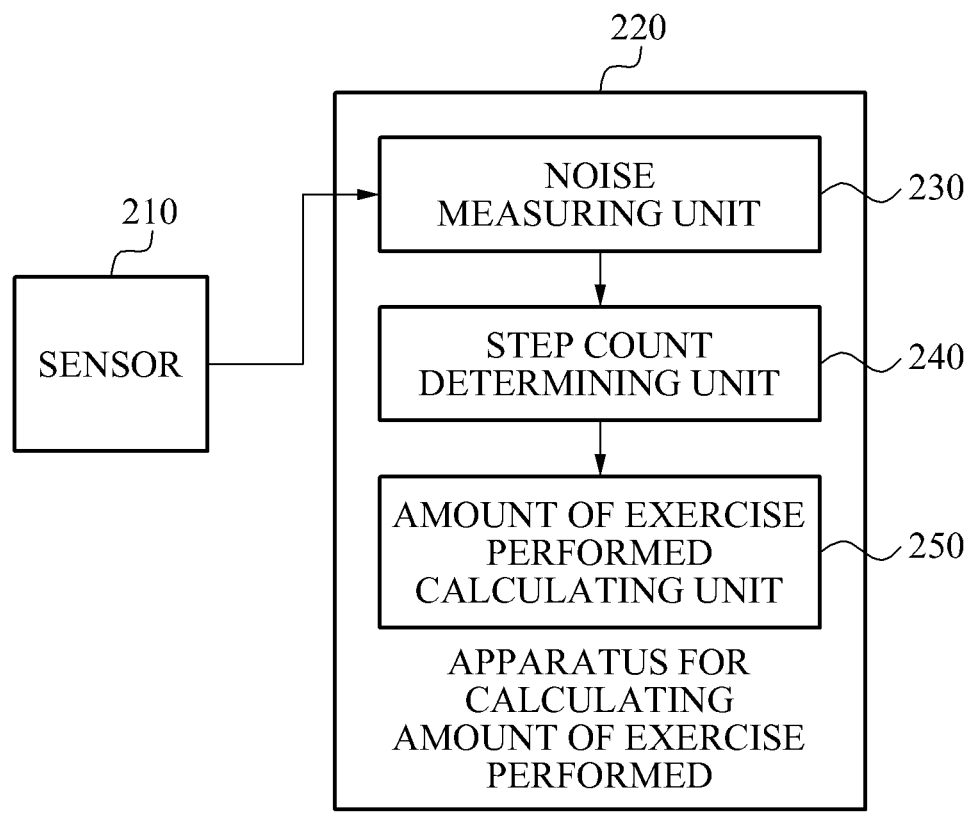
FIG. 2 is a diagram illustrating an example of a detailed configuration of an apparatus for calculating an amount of exercise performed.

FIG. 2 is a diagram illustrating an example of a detailed configuration of an apparatus 220 for calculating an amount of exercise performed. Referring to FIG. 2, the apparatus 220 for calculating the amount of exercise performed includes a noise measuring unit 230, a step count determining unit 240, and an amount of exercise performed calculating unit 250.

The noise measuring unit 230 extracts noise based on a relative difference in displacement between a skin of a user and a sensor 210 attached to the skin of the user. For example, the noise measuring unit 230 may measure noise by detecting, through the sensor 210, an HCP generated by a relative difference in displacement between the skin of the user and the sensor 210. When the sensor 210 detects the HCP, the noise measuring unit 230 may measure noise that reacts sensitively in response to a step taken by the user.

The noise measuring unit 230 measures noise by detecting an impedance change to which an electrical property change generated by a relative difference in displacement between the skin of the user and the sensor 210 attached to the skin of the user is applied. For example, the noise measuring unit 230 may measure noise by analyzing an impedance value changeable by a movement of the user, and including user movement information.

The step count determining unit 240 determines a number of steps taken by the user based on the measured noise.

The step count determining unit 240 determines the number of steps taken by the user based on noise converted to a frequency domain. For example, the step count determining unit 240 may identify a frequency of noise having a greatest value in the noise converted to the frequency domain, and determine the number of steps taken by the user based on the identified frequency and a number of steps corresponding to a single cycle of the noise.

For example, the step count determining unit 240 may convert the measured noise to a frequency domain by performing a fast Fourier transform (FFT) on the measured noise. The step count determining unit 240 may identify a frequency having a greatest value by performing a frequency analysis of the noise converted to the frequency domain. The step count determining unit 240 may determine the number of steps taken based on the frequency having the greatest value and a number of steps corresponding to a single cycle of the noise. The step count determining unit 240 may rapidly determine the number of steps taken by the user as the fast Fourier transform is performed on the measured noise.

As another example, the step count determining unit 240 may extract peaks of noise by sampling the noise, and determine a number of steps taken by a user based on a number of peaks extracted. For example, the step count determining unit 240 may extract the peaks of noise by excluding noise failing to satisfy a predetermined threshold from the sampled noise.

For example, the step count determining unit 240 may a maximum amplitude of noise and set a predetermined ratio of the maximum amplitude to be a threshold value. or may set a predetermined size of noise to be the threshold value. The step count determining unit 240 may exclude noise lower than the set threshold value from a range of extraction of peaks of noise, and extract a peak only if the noise is greater than the threshold value. The step count determining unit 240 may extract a peak more precisely by removing a noise component immaterial to a step taken by a user by excluding noise failing to satisfy the threshold.

The step count determining unit 240 may convert an analog noise signal measured by the noise measuring unit 230 to a digital noise signal using an analog-to-digital converter (ADC), and extract a peak by applying a high-pass filter (HPF) to the digital noise signal.

The step count determining unit 240 extracts a peak from sampled noise. Extracting of a peak from the sampled noise will further be described in FIG. 4. The step count determining unit 240 may determine the number of steps taken by the user based on a number of peaks extracted from the noise. For example, when the number of peaks is determined, the step count determining unit 240 may determine the number of steps taken by the user by multiplying the number of peaks by a constant value "2" representing a number of steps corresponding to a single cycle of the noise.

The amount of exercise performed calculating unit 250 calculates an amount of exercise performed by the user based on the determined number of steps. For example, the amount of exercise performed by the user may include any one or any combination of a number of steps, an amount of energy consumed, and an amount of oxygen consumed by the user during exercise.

The amount of exercise performed calculating unit 250 calculates the amount of exercise performed by the user based on physiological information of the user, such as the determined number of steps, a stride length, a weight, and other physiological information of the user. For example, the amount of exercise performed calculating unit 250 may calculate a speed at which exercise is performed by the user based on the determined number of steps, the stride length, and a duration of exercise performed by the user, and calculate the amount of exercise performed by the user based on the calculated speed at which exercise is performed by the user and the weight of the user.

In one example, the amount of exercise performed calculating unit 250 may calculate an amount of energy consumed during exercise based on an amount of exercise performed calculating model represented by the following Equation 1:

Amount of energy consumed(kilocalories(kcal))
=1.05×metabolic equivalents(METs)×duration of
exercise(minutes(min))×weight (kilograms(kg))     (1)

In Equation 1, METs (kcal/kg/minute) denotes a number of kilocalories consumed per unit time and per unit weight. METs may be calculated using the following Equation 2:

METs=0.0272×speed of exercise(meters(m)/min)+1.2     (2)

The speed of exercise in Equation 1 may be calculated based on a number of steps taken, a stride length, and a duration of exercise performed by a user during exercise using the following Equation 3:

Speed of exercise(m/min)=stride length(m)×number
of steps÷duration of exercise(min)     (3)

The amount of exercise calculating unit 250 calculates the speed of exercise and METs by applying the stride length of the user, a number of steps obtained from noise between the skin and the sensor 210, and the measured duration of exercise to the amount of exercise calculating model, and calculate an amount of energy consumed during exercise performed by the user based on the calculated METs, the duration of exercise, and the weight.

The amount of exercise performed calculating unit 250 calculates an amount of oxygen consumed during exercise using the following Equation 4 based on the speed of exercise obtained using Equation 3:

Amount of oxygen consumed(milliliter(ml))=weight
(kg)×duration of exercise(min)×amount of oxygen consumed per kilogram per minute (ml/kg/
min)     (4)

The amount of oxygen consumed per kilogram per minute in Equation 4 may be calculated using the following Equation 5:

Amount of oxygen consumed per kilogram per minute(ml/kg/min)=$a$×speed of exercise(m/min)+3.5     (5)

In Equation 5, "a" denotes a constant that varies based on a type of exercise, and the constant may be "0.1" when walking, and "0.2" when running.

The amount of exercise performed calculating unit 250 determines the number of steps taken by the user based on the measured noise, calculates the speed of exercise (the speed at which exercise is performed by the user) based on the determined number of steps, and calculates the amount of oxygen consumed during exercise based on the calculated speed of exercise.

The amount of exercise performed calculating unit 250 calculates a different amount of exercise from a single result based on a relationship between the amount of energy consumed and the amount of oxygen consumed based on experimental results. For example, in a relationship in which energy of 5 kcal is consumed when the user consumes oxygen of 1 liter (i), the amount of exercise calculating performed unit 250 may calculate the amount of energy based on the relationship with the amount of oxygen consumed.

However, the amount of exercise calculating model used by the amount of exercise performed calculating unit 250 is not limited to the amount of exercise calculating model described above, and the amount of exercise performed calculating unit 250 may use various exercise calculating models that calculate an amount of exercise performed based on the number of steps taken.

As another example, the amount of exercise performed calculating unit 250 may calculate an amount of exercise performed by a user based on a lookup table (LUT) indicating a relationship between a number of steps taken and an amount of exercise performed and the determined number of steps. The amount of exercise performed calculating unit 250 may determine a number of steps taken by the user based on the measured noise, and rapidly calculate an amount of exercise performed by extracting, from the LUT, an amount of exercise performed corresponding to the determined number of steps.

Figure 3A:
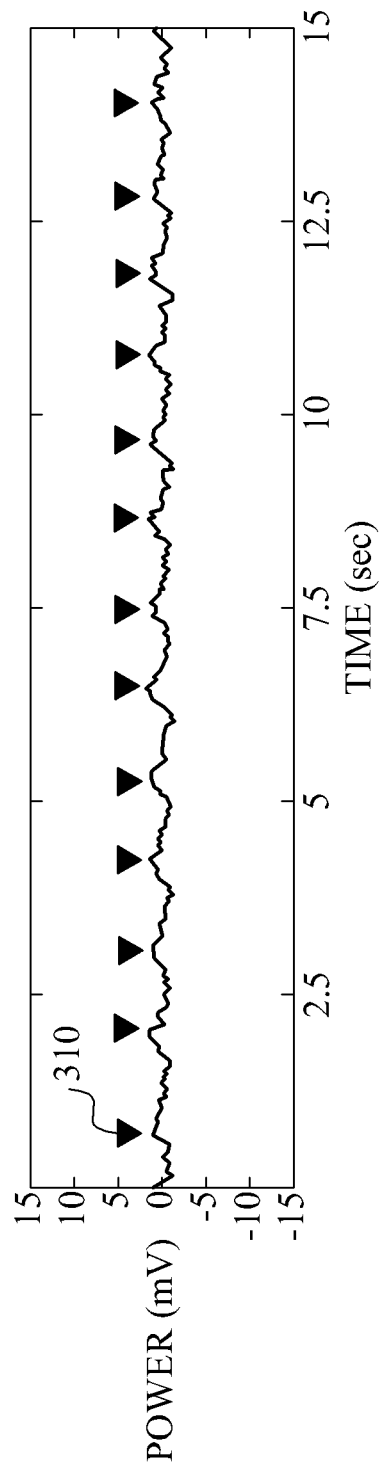

FIGS. 3A and 3B are graphs examples of noise measured from a sensor. Referring to FIGS. 3A and 3B, an example of noise measured in a form of an HCP by an apparatus for calculating an amount of exercise is illustrated. FIG. 3A illustrates an example of an HCP when a user is walking, and FIG. 3B illustrates an example of an HCP when the user is running. A peak 310 denotes the peak 310 in an HCP signal of FIG. 3A and in an HCP signal of FIG. 3B.

The apparatus for calculating the amount of exercise measures noise, generated by exercise performed by the user, between a skin of the user and a sensor attached to the skin, and the measuring of the noise is represented as an HCP signal as shown in FIGS. 3A and 3B. Comparing FIG. 3A and FIG. 3B, when the user is running, a maximum amplitude of the HCP may be greater, and a greater number of the peak 310 may be generated during an equal duration.

The apparatus for calculating the amount of exercise performed may extract the peak 310 from the noise in FIG. 3, and based on a number of peaks 310 extracted, may determine a number of steps taken by the user. The apparatus for calculating the amount of exercise may determine the number of steps taken by the user by multiplying the number of peaks 310 extracted by a constant "2", representing a number of steps corresponding to a single cycle of the noise.

Figure 4:
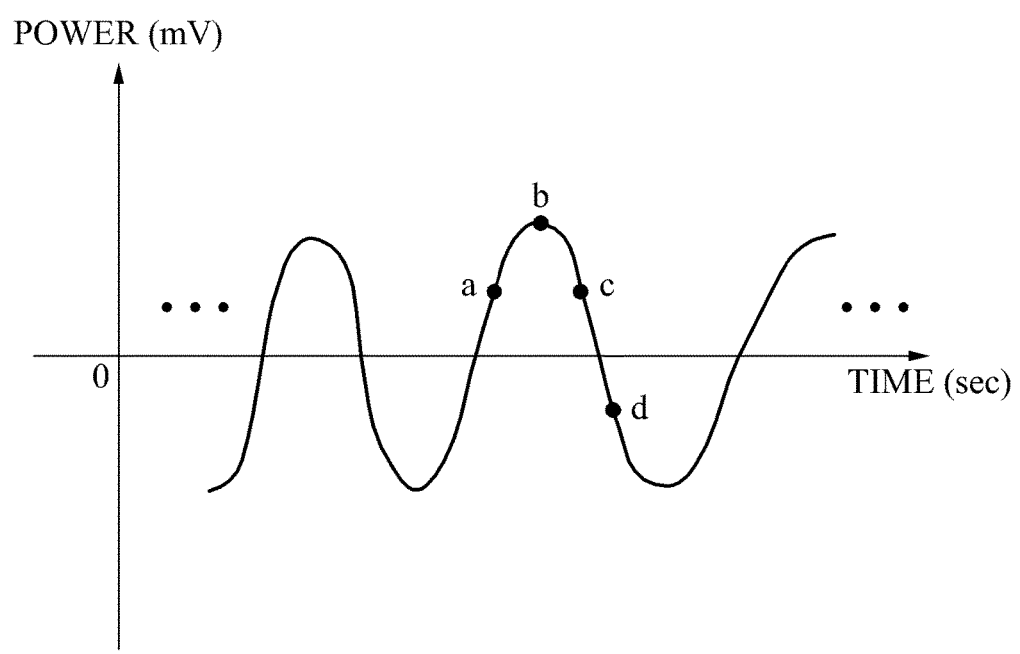
FIG. 4 is a graph illustrating an example of an operation of extracting a peak.

FIG. 4 is a graph illustrating an example of an operation of extracting a peak. In greater detail, FIG. 4 is a graph illustrating a magnified portion of noise measured in a form of an HCP in FIGS. 3A and 3B. Referring to FIG. 4, four noise values of "a", "b", "c", and "d" may be used to describe the operation of extracting the peak.

For example, an apparatus for calculating an amount of exercise may extract a peak using the following Equation 6 and three noise values:

$$\{x(t)-x(t-1)\} \times \{x(t+1)-x(t)\} < 0 \qquad (6)$$

In Equation 6, x (t−1), x (t), and x (t+1) denote, in order, noise values measured chronologically. For example, when the three noise values "a", "b", and "c" in FIG. 4 are used, x (t−1), x (t), and x (t+1) may correspond to "a", "b", and "c" sequentially. When the noise value of "b" is greater than the noise values of "a" and "c" as shown in FIG. 4, a value of (b−a)×(c−b) are negative. Accordingly, the apparatus for calculating the amount of exercise performed may extract a single peak in a section ranging from "a" to "c".

Alternatively, the apparatus for calculating the amount of exercise performed may extract a peak using the following Equation 7 and two noise values:

$$x(t) \times x(t+1) < 0 \qquad (7)$$

In Equation 7, x(t) and x(t+1) denote, in order, noise values measured chronologically. When two noise values "c" and "d" are used, x(t) and x(t+1) may correspond to "c" and "d", respectively. In FIG. 4, since the noise value of "c" is positive, and the noise value of "d" is negative, a value of (c×d) may be negative, and the apparatus for calculating the amount of exercise performed may identify a section in which a noise signal has a zero crossing on a temporal axis based on Equation 7. For example, the apparatus for calculating the amount of exercise performed may identify a zero crossing in the section ranging from "c" to "d" in FIG. 4.

The apparatus for calculating the amount of exercise performed may identify a number of peaks based on a number of zero crossings. For example, since a single peak may cause two zero crossings, the apparatus for calculating the amount of exercise may identify the number of peaks by dividing a number of zero crossings identified by a value of two. Since a single peak in noise denotes two steps, the apparatus for calculating the amount of exercise performed may determine a number of steps taken by multiplying the number of identified peaks by "2".

Figure 5A:
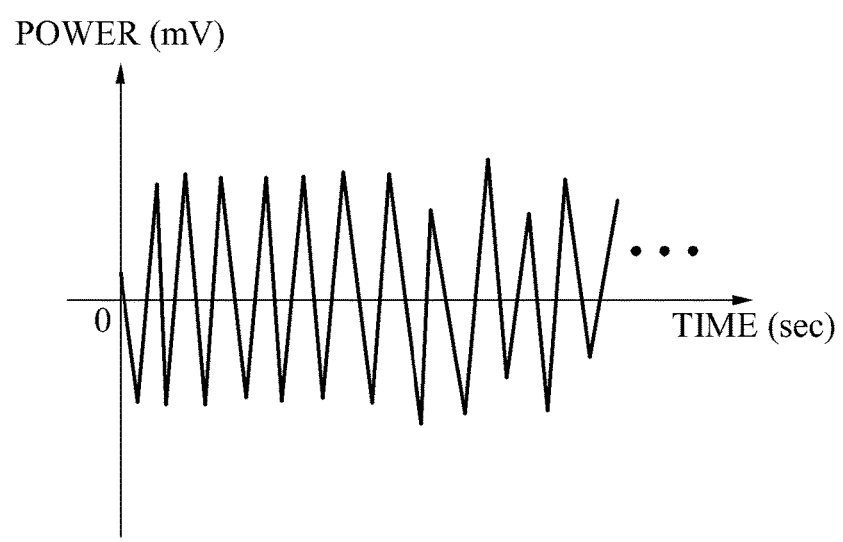
FIGS. 5A and 5B are graphs illustrating examples of an operation of deriving a number of steps taken.
Figure 5B:
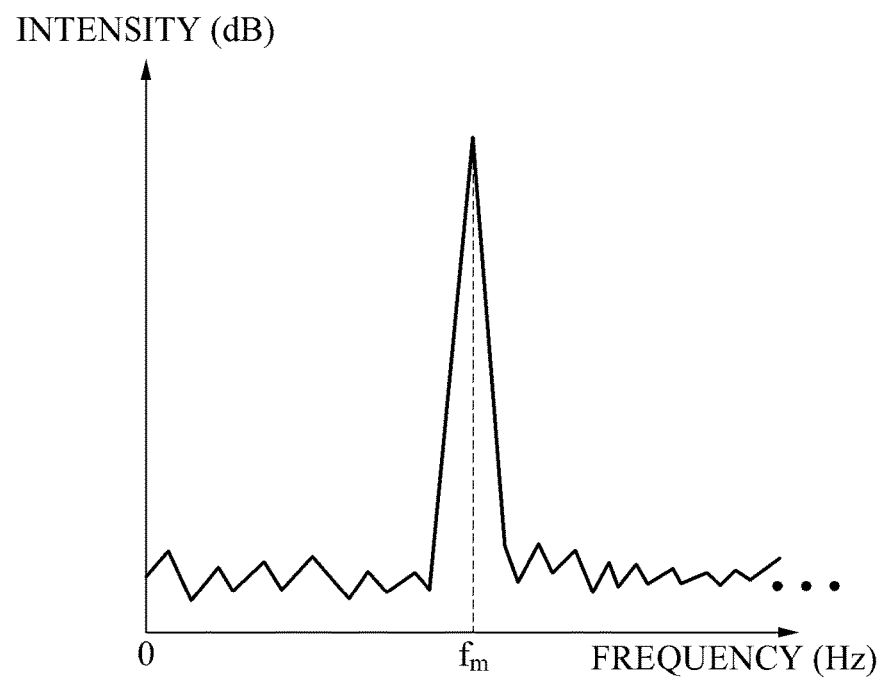

FIGS. 5A and 5B are graphs illustrating examples of an operation of deriving a number of steps taken.

FIG. 5A illustrates an example of noise measured between a skin and a sensor attached to the skin by an apparatus for calculating an amount of exercise performed. The apparatus for calculating the amount of exercise performed may convert the measured noise to a frequency domain as shown in FIG. 5B to determine a number of steps taken by the user. FIG. 5B denotes a result of conversion of the measured noise to the frequency domain by performing an FFT on the measured noise.

The apparatus for calculating the amount of exercise performed converts the noise to the frequency domain as shown in FIG. 5B, and determines a number of steps using the following Equation 8:

$$\text{Number of steps taken per minute} = f_m(\text{Hertz}) \times 60 \text{ (step/min)} \times 2 \qquad (8)$$

In Equation 8, "$f_m$" denotes a frequency of noise having a greatest value in a frequency domain. The apparatus for calculating the amount of exercise performed may determine a number of steps per minute by multiplying the identified frequency by "2", representing a number of steps corresponding to a single cycle of the noise, and a constant for a time conversion.

For example, when $f_m$ is identified as 1.453 Hz, a number of steps taken by a user may be 1.453×60×2=174.36. Accordingly, it is determined that about 175 steps are taken by the user per minute.

The apparatus for calculating the amount of exercise performed applies the determined number of steps to an amount of exercise performed calculating model to calculate a number of steps taken during exercise, an amount of energy consumed, or an amount of oxygen consumed.

Figure 6:
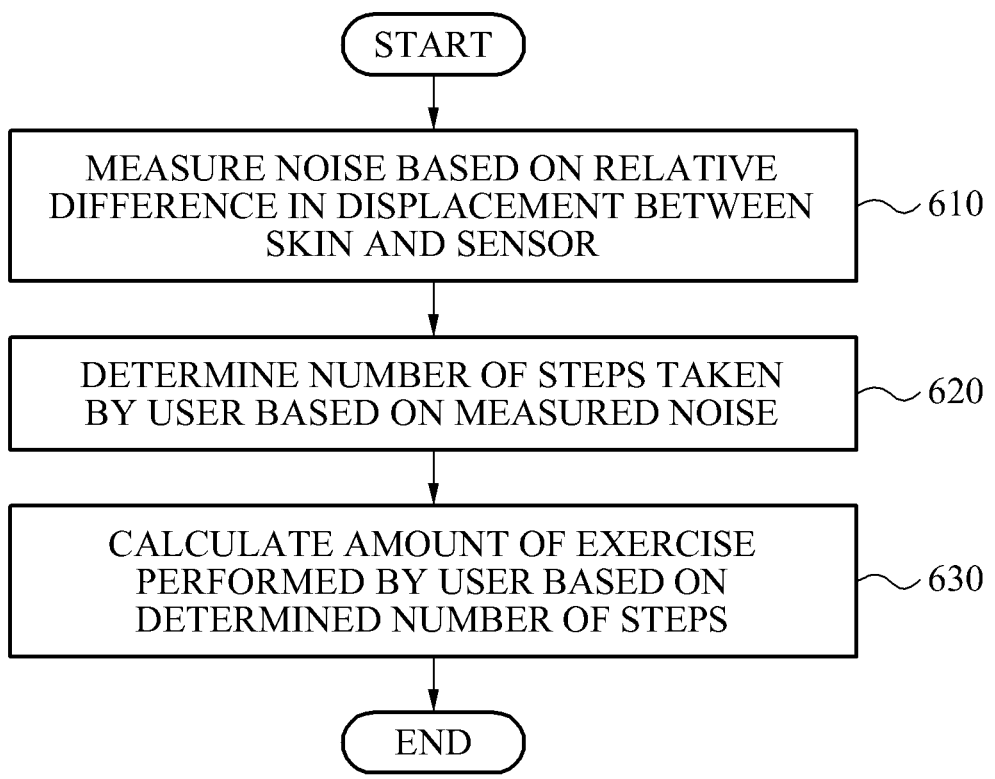
FIG. 6 is a flowchart illustrating an example of a method of calculating an amount of exercise performed.

FIG. 6 is a flowchart illustrating an example of a method of calculating an amount of exercise. In 610, an apparatus for calculating an amount of exercise performed measures noise based on a relative difference in displacement between a skin of a user and a sensor attached to the skin of the user. For example, the apparatus for calculating the amount of exercise performed may measure noise by detecting, from the sensor, an HCP generated by the relative difference in displacement between the skin of the user and the sensor. The apparatus for calculating the amount of exercise may measure noise by detecting, from the sensor, an impedance change to which an electrical property change of a skin generated by the relative difference in displacement between the skin of the user and the sensor is applied. For example, the apparatus for calculating the amount of exercise performed may measure noise by analyzing an impedance value changeable by a movement of the user, and the noise may include movement information of the user.

In 620, the apparatus for calculating the amount of exercise performed determines a number of steps taken by the user based on the measured noise. For example, the apparatus for calculating the amount of exercise performed may extract peaks of noise, and determine a number of steps taken based on a number of peaks extracted. The apparatus for calculating the amount of exercise performed may convert noise to a frequency domain, and determine a number of steps taken by performing a frequency analysis on the noise converted to the frequency domain.

In 630, the apparatus for calculating the amount of exercise performed calculates an amount of exercise performed by the user based on the determined number of steps. The amount of exercise performed by the user may include any one or any combination of a number of steps taken by the user, an amount of energy consumed, and an amount of oxygen consumed during exercise.

For example, the apparatus for calculating the amount of exercise performed calculates an amount of exercise performed by applying the determined number of steps to an amount of exercise calculating model. The apparatus for calculating the amount of exercise performed may calculate an amount of exercise performed by the user based on the determined number of steps and physiological information of the user, or calculate an amount of exercise performed by the user based on an LUT indicating a relationship between a number of steps taken and an amount of exercise performed and the determined number of steps.

Figure 7:
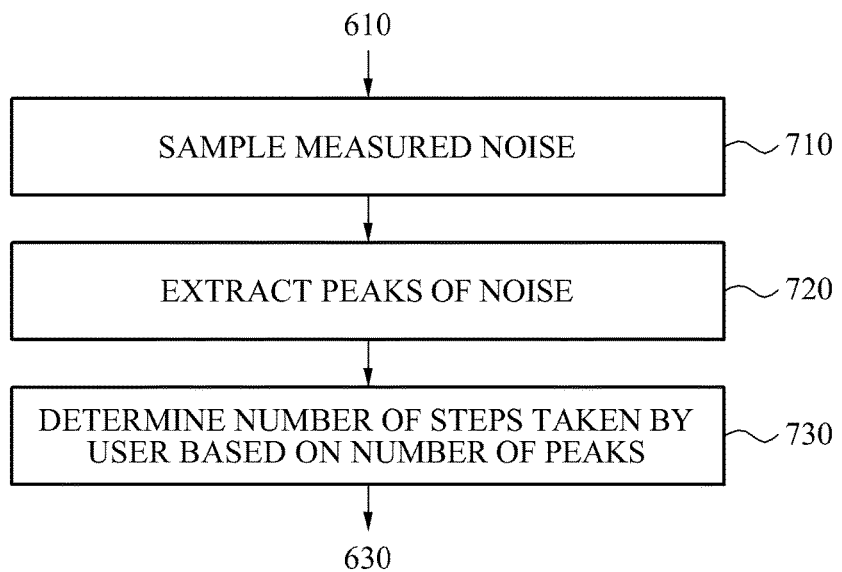
FIG. 7 is a flowchart illustrating an example of an operation of determining a number of steps taken.

FIG. 7 is a flowchart illustrating an example of an operation of determining a number of steps taken. In 710, an apparatus for calculating an amount of exercise performed samples measured noise.

In 720, the apparatus for calculating the amount of exercise performed may extract peaks of noise based on the sampled noise value. For example, the apparatus for calculating the amount of exercise performed may extract the peaks of noise by excluding noise failing to satisfy a predetermined threshold in the sampled noise.

The apparatus for calculating the amount of exercise performed may convert an analog noise signal to a digital noise signal using an ADC, and extract peaks by applying an HPF to the digital noise signal.

In 730, the apparatus for calculating the amount of exercise performed determines a number of steps taken by the user based on a number of peaks extracted. For example, when the apparatus for calculating the amount of exercise is determined, the apparatus for calculating the amount of exercise performed may determine a number of steps taken by the user by multiplying the number of peaks by a constant "2", representing a number of steps for a single cycle of the noise.

Figure 8:
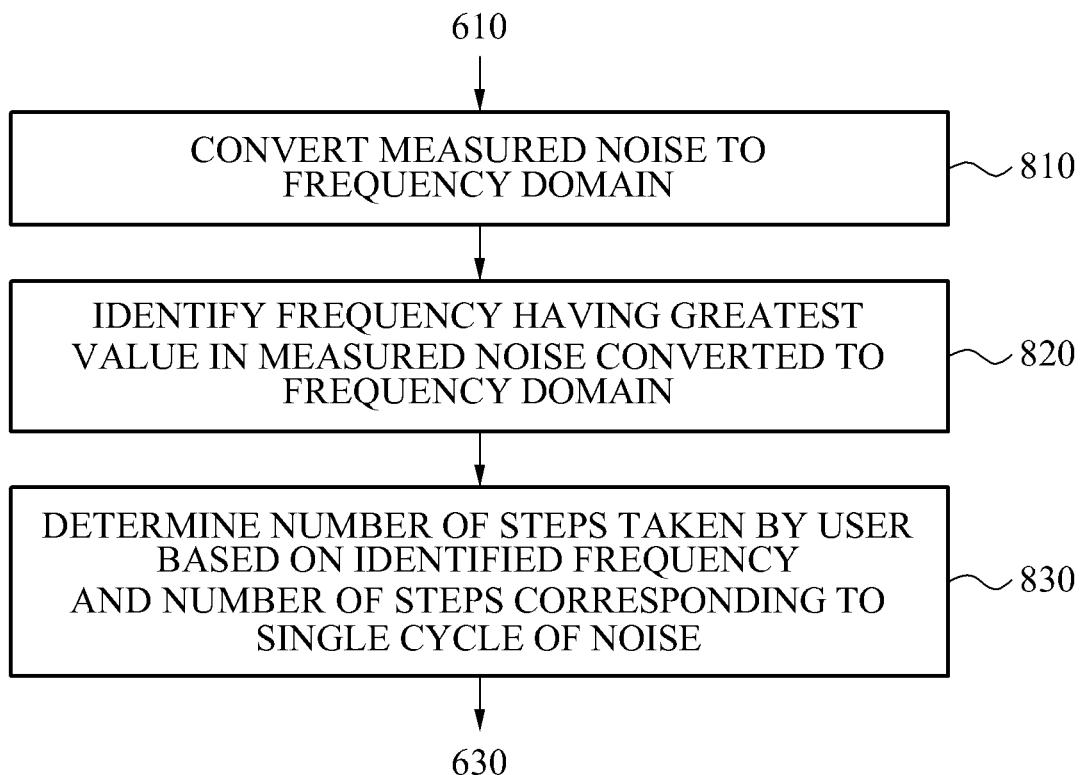
FIG. 8 is a flowchart illustrating another example of an operation of determining a number of steps taken.

FIG. 8 is a flowchart illustrating another example of an operation of determining a number of steps taken. In 810, an apparatus for calculating an amount of exercise performed converts measured noise to a frequency domain. For example, the apparatus for calculating the amount of exercise performed may convert the measured noise to the frequency domain by performing an FFT on the measured noise.

In 820, the apparatus for calculating the amount of exercise performed identifies a frequency of noise having a greatest value in the measured noise converted to the frequency domain.

In 830, the apparatus for calculating the amount of exercise performed determines a number of steps taken by the user based on the identified frequency and a number of steps taken corresponding to a single cycle of the noise. For example, the apparatus for calculating the amount of exercise performed may determine a number of steps taken per hour by multiplying the identified frequency by a value of "2", representing a number of steps corresponding to a single cycle of the noise, and a constant for time conversion.

Figure 9:
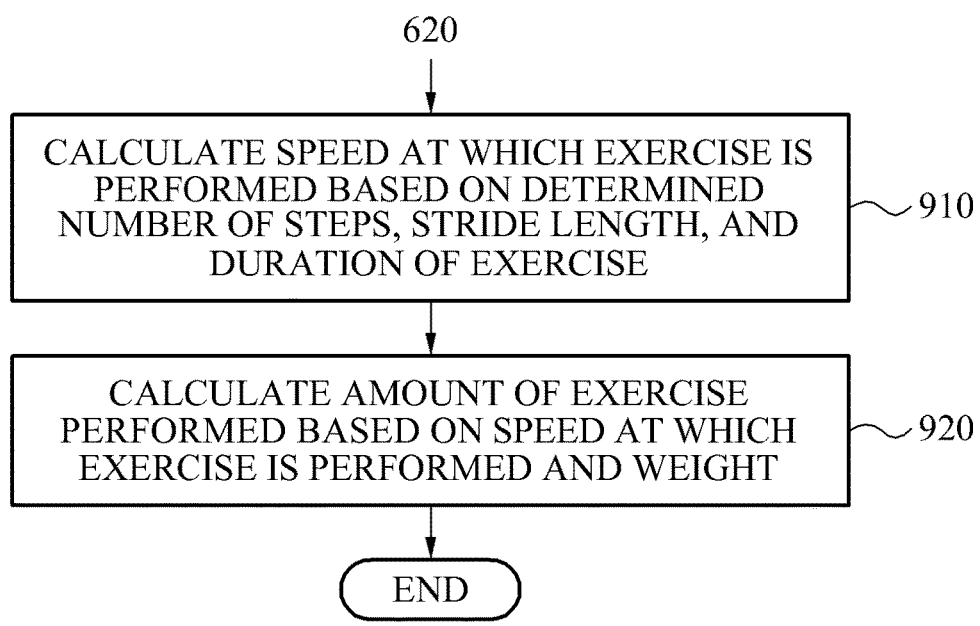
FIG. 9 is a flowchart illustrating another example of an operation of calculating an amount of exercise performed.

FIG. 9 is a flowchart illustrating another example of an operation of calculating an amount of exercise performed. In 910, an apparatus for calculating an amount of exercise performed calculates a speed at which exercise is performed by a user based on a determined number of steps taken, a stride length of the user, and a duration of exercise performed by the user. For example, the apparatus for calculating the amount of exercise performed may multiply the stride length of the user by the determined number of steps taken, and divide the result of the multiplying by the duration of exercise performed by the user to calculate a speed at which exercise is performed by the user.

In 920, the apparatus for calculating the amount of exercise performed calculates an amount of exercise performed by the user based on the calculated speed at which exercise is performed by the user and a weight of the user. For example, the apparatus for calculating the amount of exercise performed may calculate METs, representing an amount of energy consumed per unit time and unit weight based on the calculated speed at which exercise is performed, and calculate an amount of energy consumed based on the calculated METs, the weight of the user, and the duration of exercise performed by the user.

The apparatus 130 for calculating an amount of exercise performed illustrated in FIG. 1 and the apparatus 220 for calculating the amount of exercise performed, the noise measuring unit 230, the step count determining unit 240, and the amount of exercise performed calculating unit 250 illustrated in FIG. 2 that perform the operations illustrated in FIGS. 3A, 3B, 4, 5A, 5B, and 6-9 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the following claims and their equivalents are to be construed as being included in the disclosure.

What is claimed is:

1. A method of determining steps of a user, comprising:
   detecting an electrical potential, received from an electrode of a sensor mounted on the user's skin, between the electrode and the user's skin based on relative displacement between the user's skin and the electrode;
   measuring, using a processor, noise in the electrical signal, the noise being generated by a change in the electrical potential generated by a change in the relative displacement between the user's skin and the electrode; and
   determining, using the processor, steps taken by the user by analyzing the measured noise based on the change in the relative displacement between the user's skin and the electrode.

2. The method of claim 1, wherein the determining comprises:
   converting the measured noise to a frequency domain; and
   determining steps taken by the user based on the measured noise converted to the frequency domain.

3. The method of claim 2, wherein the determining steps taken by the user further comprises:
   determining a number of steps taken by the user based on a frequency of the noise having a greatest value from the noise converted to the frequency domain and a number of steps taken according to a single cycle of the noise.

4. The method of claim 1, wherein the determining comprises:
   sampling the measured noise;
   extracting peaks of the noise from the sampled noise; and
   determining steps taken by the user based on a number of the extracted peaks.

5. The method of claim 4, wherein the extracting of the peaks of the noise comprises excluding noise failing to satisfy a predetermined threshold from the sampled noise.

6. The method of claim 1, wherein the measuring of the noise comprises detecting, from the sensor, a half cell potential (HCP), and measuring potential changes in the HCP that represent the noise generated by the change in relative displacement between the user's skin and the electrode.

7. The method of claim 1, wherein the measuring of the noise comprises detecting, from the sensor, a change of impedance generated by the change of relative displacement between the user's skin and the electrode.

8. The method of claim 1, wherein the measuring of the noise comprises detecting a biological signal of the user from the sensor and measuring the noise as changes in the signal caused by motion of the user.

9. The method of claim 8, wherein the biological signal is a half cell potential (HCP) signal.

10. The method of claim 1, wherein the determining steps is performed without using an acceleration sensor.

11. A non-transitory computer readable medium storing instructions which, when executed by a processor, cause the processor to perform the method of claim 1.

12. An apparatus for determining steps taken by a user, comprising:
    a sensor mounted on the user's skin, and configured to detect an electrical potential between an electrode of the sensor and the user's skin based on relative displacement between the user's skin and the electrode;
    a noise measuring processor configured to measure noise in an electrical signal received from the sensor, the noise being generated by a change of the electrical potential generated by a change of the relative displacement between the user's skin and the electrode; and
    a determining processor configured to determine steps taken by the user by analyzing the measured noise based on the change in the relative displacement between the user's skin and the electrode.

13. The apparatus of claim 12, wherein the determining processor is further configured to:
convert the measured noise to a frequency domain; and
determine steps taken by the user based on the noise converted to the frequency domain.

14. The apparatus of claim 12, wherein the determining processor is further configured to determine steps taken by the user without using an acceleration sensor.

15. The apparatus of claim 12, wherein the noise measuring processor is further configured to measure the noise by detecting, from the sensor, a half cell potential (HCP) generated by the change in the relative displacement between the user's skin and the electrode.

16. The apparatus of claim 12, wherein the noise measuring processor is further configured to measure the noise by detecting, from the sensor, a change of impedance generated by the change of the relative displacement between the user's skin and the electrode.

17. A method of determining steps taken by a user, comprising:
detecting an electrical potential, received from an electrode of a sensor mounted on the user's skin, between the electrode and the user's skin based on relative displacement between the user's skin and the electrode;
measuring, using a processor, noise in the electrical signal generated based on a change of the electrical potential generated by movement of the user while performing exercise; and
determining, using the processor, steps taken by the user by analyzing the measured noise based on the change of the electrical potential generated by the movement of the user.

18. The method of claim 17, wherein the measuring comprises measuring the noise while the sensor is attached to the user's skin; and
the noise is represented by changes in the electrical signal received from the sensor that are generated based on relative movement between the electrode and the user's skin resulting from the movement of the user while performing exercise.

19. The method of claim 17, wherein the determining steps taken comprises:
extracting information from the measured noise; and
determining steps taken by the user based on the extracted information.

20. A non-transitory computer readable medium storing instructions which, when executed by a processor, cause the processor to perform the method of claim 17.

* * * * *